(12) United States Patent
Ahlquist et al.

(10) Patent No.: US 7,785,772 B2
(45) Date of Patent: Aug. 31, 2010

(54) DETECTING METHYLATED MAMMALIAN NUCLEIC ACID IN STOOL

(75) Inventors: David A. Ahlquist, Rochester, MN (US); Hongzhi Zou, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 12/018,273

(22) Filed: Jan. 23, 2008

(65) Prior Publication Data

US 2008/0220433 A1 Sep. 11, 2008

Related U.S. Application Data

(60) Provisional application No. 60/886,278, filed on Jan. 23, 2007.

(51) Int. Cl.
*C12Q 1/00* (2006.01)
*G01N 33/53* (2006.01)

(52) U.S. Cl. ............................................. 435/4; 435/7.1
(58) Field of Classification Search .................. None
See application file for complete search history.

(56) References Cited

OTHER PUBLICATIONS

Shiraishi et al (Analytical Biochemistry, Jun. 2004, 329(1):1-10).*
Belshaw et al (Cancer Epidemiology and Prevention, Sep. 2004, 13(9): 1495-1501).*
Ueki et al (Cancer Research, Apr. 2000, 60:1835-1839).*
Caldas et al (Cancer Research, Jul. 1994, 54: 3568-3573).*
Ahlquist et al., "Colorectal Cancer Screening by Detection of Altered Human DNA in Stool: Feasibility of a Multitarget Assay Panel," *Gastroenterology*, 2000, 119:1219-1227.
Ahlquist et al., "Novel Use of Hypermethylated DNA Markers in Stool for Detection of Colorectal Cancer: A Feasibility study," *Gastroenterology*, 2002, 122:Suppl A40.
Belshaw et al., "Use of DNA from Human Stools to Detect Aberrant CpG Island Methylation of Genes Implicated in Colorectal Cancer," *Cancer Epidemiol. Biomarkers Prev.*, 2004, 13:1495-1501.
Bird, "CpG-rich islands and the function of DNA methylation," *Nature*, 1986, 321:209-213.
Chen et al., "Detection in Fecal DNA of Colon Cancer-Specific Methylation of the Nonexpressed Vimentin Gene," *J. Natl. Cancer Inst.*, 2005, 97(15):1124-1132.
Cross et al., "Purification of CpG islands using a methylated DNA binding column," *Nat Genet.*, 1994, 6:236-244.
Gardiner-Garden and Frommer, CpG Islands in "Vertebrate Genomes," *J. Mol. Biol.*, 1987, 196:261-282.
Jemal et al., "Cancer Statistics, 2006," *CA Cancer J. Clin.*, 2006, 56:106-130.
Klimasauskas et al., "HhaI Methyltransferase Flips Its Target Base Out of the DNA Helix," *Cell*, 1994, 76:357-369.
Landis et al., "Cancer Statistics, 1998," *CA Cancer J. Clin.*, 1998, 48:6-29.
Lengauer et al., "DNA methylation and genetic instability in colorectal cancer cells," *Proc. Natl. Acad. Sci. USA*, 1997, 94:2545-2550.
Lenhard et al., "Analysis of Promoter Methylation in Stool: A Novel Method for the Detection of Colorectal Cancer," *Clin. Gastroenterol. Hepatol.*, 2005, 3:142-149.
Leung et al., "Detection of Epigenetic Changes in Fecal DNA as a Molecular Screening Test for Colorectal Cancer: A Feasibility Study," *Clin. Chem.*, 2004, 50:2179-2182.
Müller et al., "Methylation changes in faecal DNA: a marker for colorectal cancer screening?" *Lancet*, 2004, 363:1283-1285.
Nan et al., "Dissection of the methyl-CpG binding domain from the chromosomal protein MeCP2," *Nucleic Acids Res.*, 1993, 21(21):4886-4892.
Osborn and Ahlquist, "Stool Screening for Colorectal Cancer: Molecular Approaches," *Gastroenterology*, 2005, 128:192-206.
Palmer and Marinus, "The *dam* and *dcm* strains of *Escherichia coli*—a review," *Gene*, 1994, 143:1-12.
Petko et al., "Aberrantly Methylated *CDKN2A*, *MGMT*, and *MLH1* in Colon Polyps and in Fecal DNA from Patients with Colorectal Polyps," *Clin. Cancer Res.*, 2005, 11:1203-1209.
Shiraishi et al., "Isolation of DNA fragments associated with methylated CpG islands in human adenocarcinomas of the lung using a methylated DNA binding column and denaturing gradient gel electrophoresis," *Proc Natl. Acad. Sci. USA*, 1999, 96:2913-2918.
Whitney et al., "Enhanced Retrieval of DNA from Human Fecal Samples Results in Improved Performance of Colorectal Cancer Screening Test," *J. Mol. Diagn.*, 2004, 6(4):386-395.
Zijlstra et al., "A Quantitative Analysis of Rate-limiting Steps in the Metastatic Cascade Using Human-specific Real-Time Polymerase Chain Reaction," *Cancer Res.*, 2002, 62:7083-7092.
Zou et al., "A Sensitive Method to Quantify Human Long DNA in Stool: Relevance to Colorectal Cancer Screening," *Cancer Epidemiol. Biomarkers Prev.*, 2006, 15(6):1115-1119.
Zou et al., "Frequent Methylation of *Eyes Absent 4* Gene in Barrett's Esophagus and Esophageal Adenocarcinoma," *Cancer Epidemiol. Biomarkers Prev.*, 2005, 14(4):830-834.

* cited by examiner

*Primary Examiner*—Sean E Aeder
(74) *Attorney, Agent, or Firm*—Casimir Jones SC

(57) ABSTRACT

This document includes methods and materials for enriching and detecting cancer markers. For example, this document includes methods and materials for enriching methylated mammalian nucleic acid from stool samples.

11 Claims, 1 Drawing Sheet

DETECTING METHYLATED MAMMALIAN NUCLEIC ACID IN STOOL

CROSS-REFERENCE TO RELATED APPLICATIONS

This application claims the benefit of U.S. Provisional Application Ser. No. 60/886,278, filed on Jan. 23, 2007.

BACKGROUND

1. Technical Field

This document relates to methods and materials involved in detecting methylated mammalian nucleic acid (e.g., methylated human DNA) in stool.

2. Background Information

About half of all cancer deaths in the United States result from aerodigestive cancer. For example, of the estimated 564,800 annual cancer deaths, 160,100 (25%) result from lung cancer; 56,500 (10%) result from colorectal cancer; 28,900 (6%) result from pancreas cancer; 13,700 (3%) result from stomach cancer; and 11,900 (3%) result from esophagus cancer. In addition, over seven percent of the annual cancer deaths result from other aerodigestive cancers such as naso-oro-pharyngeal, bile duct, gall bladder, and small bowel cancers (Landis et al., *CA Cancer J. Clin.* 48:6-29 (1998)).

SUMMARY

This document relates to methods and materials involved in detecting methylated mammalian nucleic acid (e.g., methylated human DNA) in stool. For example, this document provides methods and materials that can be used to enrich methylated mammalian DNA from a stool sample so that it can be detected, even though the sample may contain large amounts of non-methylated mammalian DNA and/or methylated bacterial DNA. Assaying for methylated mammalian DNA markers (e.g., methylated human DNA markers) in stool can be used to screen for aerodigestive cancers (e.g., colonic or supracolonic digestive cancer). The detection of a methylated mammalian DNA marker in a mammal's stool can allow a clinician to diagnose cancer or pre-cancerous conditions (e.g., curable stage cancer). In addition, the analysis of a stool sample is much less invasive than other types of diagnostic techniques such as endoscopy.

This document is based, in part, on the discovery that the methods and materials provided herein can be used to enrich methylated mammalian nucleic acid markers (e.g., markers originating from a neoplasm located, for example, in a mammal's small intestine, gall bladder, bile duct, pancreas, liver, stomach, esophagus, lung, or naso-oro-pharyngeal airways) present in a stool sample having methylated bacterial nucleic acid so that the markers can be detected and mammals can be identified as having cancer. Once a particular mammal is determined to have stool containing a methylated mammalian nucleic acid marker, additional cancer screening techniques can be used to identify the exact location and nature of the neoplasm. For example, a stool sample can be treated as described herein to enrich methylated mammalian nucleic acid, if present. After enrichment, the sample can be analyzed to determine if the patient may have a neoplasm. Magnetic resonance imaging (MRI), endoscopic analysis, and tissue biopsy techniques can be used to identify the exact location and nature of the neoplasm. Thus, this document provides methods and materials that can be conveniently used to screen patients for cancer.

The enrichment methods and materials can be used as a universal capture means for isolating methylated human DNA sequences from stool. Such methods and materials can involve using a methyl-CpG binding domain (MBD) polypeptide. For example, an MBD polypeptide can be produced to contain a polyhistidine tag, and can be bound to a column (e.g., a nickel-agarose resin). Such a MBD column can extract methylated human DNA in a high background of fecal bacterial DNA. Enrichment of methylated mammalian nucleic acid can increase assay sensitivity for detecting methylated DNA markers in stool.

In general, one aspect of this document features a method for enriching methylated mammalian nucleic acid if present in a stool sample. The method comprises, or consists essentially of, (a) contacting nucleic acid from a stool sample with an MBD polypeptide to form a nucleic acid-MBD polypeptide complex and (b) obtaining methylated mammalian nucleic acid from the complex if the stool sample contained methylated mammalian nucleic acid, thereby forming an enriched, methylated mammalian nucleic acid sample. The MBD polypeptide can be a human or rat MBD polypeptide. The enriched, methylated mammalian nucleic acid sample can comprise a higher ratio of methylated mammalian nucleic acid to methylated bacterial nucleic acid than the ratio of methylated mammalian nucleic acid to methylated bacterial nucleic acid present in the stool sample.

In another aspect, this document features a method for detecting a colorectal or supracolonic aerodigestive neoplasm in a mammal. The method comprises, or consists essentially of, (a) contacting nucleic acid from a stool sample from the mammal with an MBD polypeptide to form a nucleic acid-MBD polypeptide complex, (b) obtaining methylated mammalian nucleic acid from the complex if the stool sample contained methylated mammalian nucleic acid, thereby forming an enriched, methylated mammalian nucleic acid sample if the stool sample contained methylated mammalian nucleic acid, and (c) determining whether or not the enriched, methylated mammalian nucleic acid sample comprises a methylated mammalian nucleic acid marker indicative of the colonic or supracolonic aerodigestive neoplasm, wherein the presence of the marker indicates that the mammal has the colonic or supracolonic aerodigestive neoplasm. The neoplasm can comprise a premalignant neoplasm. The neoplasm can comprise a malignant neoplasm. The neoplasm can be a colorectal neoplasm. The neoplasm can be a supracolonic aerodigestive neoplasm. The supracolonic aerodigestive neoplasm can be selected from the group consisting of small intestine, gall bladder, bile duct, pancreas, liver, stomach, esophagus, lung, tracheal-bronchial, and naso-oro-pharyngeal neoplasms. The methylated mammalian nucleic acid marker can correspond to sequences from a gene selected from the group consisting of p16, MGMT, MLH1, BMP3, EYA2, ALX4, and vimentin.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the descrip-

DETAILED DESCRIPTION

Figure 1:
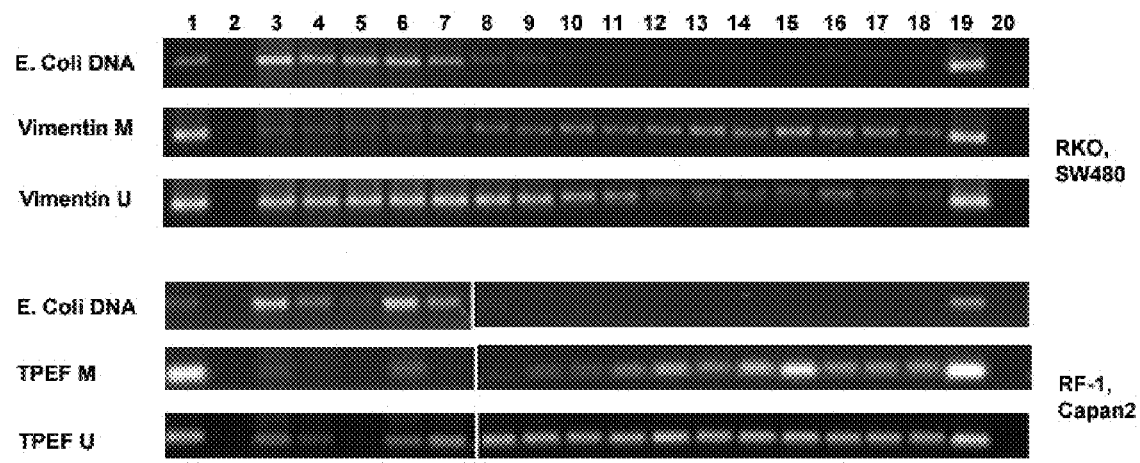
FIG. 1 is a photograph of gel demonstrating the separation of methylated DNA from a high background of bacterial DNA with a MBD column. After being digested with Mse I, 5 µg of cancer cell DNA from a methylated and an unmethylated cell line (2.5 µg each; RKO with SW480, or RF-1 with Capan2) and 50 µg stool DNA were loaded on an MBD column and eluted in MBD buffers with 0.2 to 1.0 M NaCl (5 mL each). DNA in each elute was amplified with primers specific to E. coli DNA, methylated (M) DNA, and unmethylated (U) DNA sequences. Lane 1, Flow through; Lane 2, MBD buffer/0.2 M; Lanes 3 to 18, MBD buffers with stepwise gradient of NaCl (0.4 to 1.0 M by 40 mM per step); Lane 19, Positive control; Lane 20, Water control.

This document provides methods and materials related to detecting neoplasm-specific markers in a stool sample from a mammal. For example, this document provides methods and materials for enriching and detecting methylated nucleic acid markers in a stool sample from a mammal having colon cancer or supracolonic aerodigestive cancer (e.g., cancer of the small intestine, gall bladder, bile duct, pancreas, liver, stomach, esophagus, or lung, or a naso-oro-pharyngeal cancer). It will be appreciated that the methods and materials provided herein can be used to detect a DNA methylation marker in a mammal having a combination of different neoplasms. For example, the methods and materials provided herein can be used to detect a mammalian DNA methylation marker in a human having lung and stomach neoplasms. The term "neoplasm" as used herein refers to any new and abnormal growth of tissue. Thus, a neoplasm can be a premalignant neoplasm or a malignant neoplasm.

While not being limited to a particular mode of action, this document is based, in part, on the knowledge that premalignant and malignant neoplasms arising in a mammal's small intestine, gall bladder, bile duct, pancreas, liver, stomach, esophagus, lung, or naso-oro-pharyngeal airways can shed cells into the aerodigestive lumen. These exfoliated cells as well as their constituents can survive transit through the gastrointestinal tract and ultimately pass as fecal waste. As described herein, for example, a methylated mammalian DNA marker present in a stool sample can be enriched and detected.

As used herein, a "methylated mammalian nucleic acid marker" is a mammalian nucleic acid sequence that is methylated (e.g., hypermethylated or hypomethylated) in certain conditions (e.g., cancer) as compared to the methylation status of the same mammalian nucleic acid under normal conditions (e.g., in an individual that does not have cancer). Hypermethylated DNA markers can be particularly useful for detecting colonic and supracolonic aerodigestive cancers. Such hypermethylated DNA markers can include, for example, CpG sequences from the cyclin-dependent kinase inhibitor 2A gene (p16), the methyl-guanine-DNA methyltransferase gene (MGMT), the mismatch repair gene MLH1, BMP3, EYA2, ALX4, and vimentin.

DNA methylation does not alter the coding function of a DNA, but has the potential to alter gene expression and thus can have profound developmental and genetic consequences. DNA methylation occurs at target cytosine residues that are found within CpG dinucleotides. The methylation reaction involves flipping a target cytosine out of an intact double helix to allow the transfer of a methyl group from S-adenosylmethionine to form 5-methylcytosine (Klimasauskas et al., *Cell* 76:357-369 (1994)). Areas of the genome containing long repeats of CpG dinucleotides are referred to as "CpG islands" (Bird, *Nature* 321:209-213 (1986) and Gardiner-Garden et al., *J. Mol. Biol.*, 196:261-282 (1987)). CpG islands typically are between 0.2 to about 1 kb in length and are located upstream of many genes, but may also extend into gene coding regions.

Methylation of cytosine residues contained within CpG islands of certain genes typically correlates inversely with gene activity. Methylation can lead to decreased gene expression by a variety of mechanisms including, without limitation, disruption of local chromatin structure, inhibition of DNA binding by transcription factors, or by recruitment of proteins that interact specifically with methylated sequences and thus indirectly prevent transcription factor binding. Hypermethylation of CpG islands within tumor suppressor genes therefore can lead to progressive reduction of normal tumor suppressor expression, resulting in the selection of a population of cells having a selective growth advantage (i.e., neoplasm). Alterations in normal methylation processes also can be associated with genomic instability (see, e.g., Lengauer et al., *Proc. Natl. Acad. Sci. USA*, 94:2545-2550 (1997)). Such abnormal epigenetic changes may be found in many types of cancer and can therefore serve as potential markers for oncogenic transformation.

The methods and materials provided herein can be used to obtain a sample containing methylated mammalian nucleic acid enriched from a stool sample. For example, an MBD polypeptide can be used to capture methylated mammalian nucleic acid. In some cases, an MBD polypeptide can be produced to contain a polyhistidine tag, and can be bound to a column (e.g., a nickel-agarose resin). Elution conditions can be used to optimize the amount of methylated mammalian nucleic acid recovered versus the amount of methylated bacterial nucleic acid and unmethylated nucleic acid.

Once a sample enriched for methylated mammalian nucleic acid from stool is obtained, any suitable method can be used to detect a DNA methylation markers in that enriched sample. Such methods can include isolating DNA from the sample, separating out one or more particular regions from the total DNA (e.g., CpG islands), subjecting the DNAs to bisulfite treatment, and determining whether the separated DNAs are abnormally methylated (e.g., hypermethylated). It is noted that a single sample can be analyzed for one DNA methylation marker or for multiple DNA methylation markers. For example, a sample can be analyzed using assays that detect a panel of different DNA methylation markers. In addition, multiple samples can be collected from a single mammal and analyzed as described herein. In some cases, PCR techniques can be used to detect the presence or absence of a methylated mammalian nucleic acid marker.

The invention will be further described in the following examples, which do not limit the scope of the invention described in the claims.

EXAMPLES

Example 1

Capturing Methylated Human DNA from Stool for Colorectal Cancer Screening

Methods and Materials

Cell lines. Four human digestive cancer cell lines were used, including two colon cancer cell lines (RKO and SW480), one gastric cancer cell line (RF-1), and one pancreatic cancer cell line (Capan2). RKO was grown in RPMI 1640 medium, SW480 and RF-1 were grown in Leibovitz's L-15 medium, and Capan2 was grown in Dulbecco's modified Eagle's medium. Media were supplemented with 10% fetal bovine serum, 100 U/mL of penicillin, 100 mg/mL of streptomycin, and 2 mM of L-glutamine. Cells were incubated at 37° C. in the presence of 5% $CO_2$.

Tissue and stool samples. Fourteen paraffin-embedded colon cancer tissues were used to check the methylation status of vimentin in tumor. Stools from eight patients with a corresponding methylated tumor were selected to test a methyl-CpG binding domain (MBD) column. Stools from six colonoscopically-normal individuals were used as controls. All stools were collected before colonoscopy or surgery. None of the colorectal cancer (CRC) patients had undergone chemotherapy or radiotherapy prior to stool collection. Any previous instrumentation or cathartic preparation had occurred more than two weeks before stool collection. A plastic bucket device was used to collect whole stool. Stools in sealed buckets were immediately transported to the laboratory and stored at −80° C.

DNA extraction. Tissue sections were examined by a pathologist who circled histologically distinct lesions to direct careful microdissection. Genomic DNA from both microdissected tissues and cell lines was extracted using Qiagen DNA Mini Kit (Qiagen, Valencia, Calif.). Stool was homogenized in ASL buffer (1 g stool:10 mL buffer), and extracted with QIAamp® DNA Stool Mini Kit (Qiagen).

Bisulfite treatment. Sodium bisulfite converts unmethylated cytosine residues, but not methylated cytosine residues, to uracil. DNA from tissue, cell line, and total stool was bisulfite modified using the EZ DNA Methylation Kit (Zymo Research, Orange, Calif.). Since stool DNA samples after capture with MBD column typically contains less than 1 µg DNA, whole DNA purified from each MBD elute was bisulfite modified. Thirty µL of buffer was used to elute bisulfite modified tissue and cell line DNA, and 10 µL was used for stool DNA.

Methylation-specific PCR (MSP). Bisulfite-modified DNA (1 µL for tissue and cell DNA, and 4 µL for stool DNA) was amplified in a total volume of 25 µL containing 1×PCR buffer, 1.5 mM $MgCl_2$, 200 µM of each dNTP, 400 nM of each primer, and 1.25 units of AmpliTaq Gold polymerase (Applied Biosystem). Amplification included a hot start at 95° C. for 12 minutes, 35 cycles for tissue and cell DNA or 40 cycles for stool DNA at 95° C. for 45 seconds, annealing temperatures for 45 seconds, 72° C. for 45 seconds, and a final 10-minute extension step at 72° C. The methylation-specific primers for vimentin were 5'-TCGTTTCGAG-GTTTTCGCGTTAGAGAC-3' (sense; SEQ ID NO:1) and 5'-CGACTAAAACTCGACCGACTCGCGA-3' (antisense; SEQ ID NO:2), and the annealing temperature was 68° C. (Chen et al., J. Nat'l. Cancer Inst., 97:1124-32 (2005)). The unmethylation-specific primers for vimentin were 5'-TTG-GTGGATTTTTTGTTGGTTGATG-3' (sense; SEQ ID NO:3) and 5'-CACAACTTACCTTAACCCTTAAAC-TACTCA-3' (antisense; SEQ ID NO:4), and the annealing temperature was 60° C. The methylation-specific primers for TPEF were 5'-CGGTAAAGATTCGAGTAAGGAACGT-3' (sense; SEQ ID NO:5) and 5'-AAAACATCGACCGAA-CAACGACGTC-3' (antisense; SEQ ID NO:6), and the annealing temperature was 65° C. The unmethylation-specific primers for TPEF were 5'-GTTATTTGGTAAA-GATTTGAGTAAGGAATG-3' (sense; SEQ ID NO:7) and 5'-AAAACATCAACCAAACAACAACATC-3' (antisense; SEQ ID NO:8), and the annealing temperature was 60° C. Bisulfite-treated human genomic DNA and in vitro methylated DNA were used as positive controls for unmethylation and methylation, respectively.

Preparation of MBD column. An MBD column was prepared as described elsewhere (Cross et al., Nat. Genet., 6:236-44 (1994)). MBD polypeptide tagged with six histidines was expressed from a pET6HMBD plasmid containing a MBD encoding DNA. This plasmid was obtained from Dr. Adrian Bird, Welcome Trust Centre for Cell Biology, University of Edinburgh, which was cloned from a rat MeCP2 gene (Cross et al., Nat. Genet., 6:236-44 (1994)). Briefly, MBD polypeptides were produced in BL21 star (DE3) pLysS (Invitrogen, Carlsbad, Calif.), and partially purified with a cation exchange resin, Fractogel® EMD $SO_3^-$ (M) (EMD Chemicals Inc., Gibbstown, N.J.), in a Econo-Pac Column (BioRad, Hercules, Calif.). MBD polypeptides were then coupled to a Ni-NTA Superflow (Qiagen), a nickel agarose gel that specifically binds to polypeptides tagged with six histidines, in a 10 mL Poly-Prep Chromatography Column (BioRad) to generate an MBD column. About 10 mg of MBD polypeptide was coupled per mL Ni-NTA Superflow.

Sample preparation. Stool DNA and cancer cell DNA to be loaded on the MBD column for separation were first digested overnight with Mse I (4 units/µg), which recognizes the sequence TTAA, keeping the majority of CpG islands intact, but cutting other genomic regions into short fragments. Digested DNA was then extracted with phenol/chloroform/isoamyl alcohol (25:24:1), precipitated in ethanol, and eluted in nuclease-free water.

Testing specificity of MBD binding. To test whether the MBD column separates methylated DNA from a high background of bacterial DNA, 5 µg of cancer cell DNA and 50 µg of stool DNA (all Mse I cut) were loaded on the MBD column in MBD buffer/0.1 M NaCl (20 mM HEPES, PH7.9, 10% glycerol, 0.1% Triton X-100, 0.1 M NaCl). The cancer cell DNA, which was used to simulate DNA exfoliated from cancers in digestive tract, was from a methylated cell line and an unmethylated cell line (2.5 µg each; RKO with SW480, or RF-1 with Capan2). Vimentin is methylated in RKO, but not SW480. TPEF is methylated in RF-1, but not Capan2. DNA fragments bound on MBD polypeptides were eluted using MBD buffers with gradient concentrations (0.2~1.0 M) of NaCl.

Each elute (5 mL) from the MBD column was concentrated with Amicon Ultra Centrifugal Filter Devices (30,000 MWCO, Millipore, Billerica, Mass.) to 200 μL, and then extracted with phenol/chloroform/isoamyl alcohol (25:24:1), precipitated in ethanol, and eluted in nuclease-free water. DNA from each elute was amplified with primers specific to E. Coli DNA, or bisulfite-treated for methylation analysis.

E. Coli, a common bacterium in human stool, was employed to represent fecal bacteria. Two sets of primers were designed to amplify E. Coli DNA, including one set targeting dnaK gene and the other one targeting a randomly selected undefined region. The primers specific for dnaK gene were 5'-GTGCCGGATTAGCCAACTTA-3' (sense; SEQ ID NO:9) and 5'-GTGACGATTCCAGCCGTACT-3' (antisense; SEQ ID NO:10), and the primers for the undefined E. Coli DNA region were 5'-ACTCCTGCGAAACAT-CATCC-3' (sense; SEQ ID NO:11) and 5'-CGGCACCT-TGCTAAGTCTTC-3' (antisense; SEQ ID NO:12). One μL of total stool DNA was amplified in a total volume of 25 μL containing 1×iQ™ Supermix (BioRad), 200 nM each primer under the following conditions: 95° C. for 3 minutes, followed by 28 cycles of 95° C. for 30 seconds, 60° C. for 30 seconds, and 72° C. for 40 seconds, and a final 10-minute extension step at 72° C.

Capture of cancer cell DNA spiked into stools. To test the sensitivity of an MBD column to capture methylated DNA in stool model, trace amounts of cancer cell DNA (0, 2, 10, and 50 ng; RKO with SW480) were spiked into stool aliquots (1 g each) from a homogenized normal stool. Stool DNA was extracted and digested, as above. Whole DNA from each stool aliquot was loaded on the MBD column in MBD buffer/0.52 M NaCl. Loosely bound DNA was washed away in MBD buffer/0.6 M NaCl. Tightly bound DNA was eluted in MBD buffer/1.0 M NaCl, concentrated, extracted, and bisulfite-treated for methylation analysis targeting tumor-specific methylated vimentin gene (Chen et al., J. Nat'l. Cancer Inst., 97:1124-32 (2005)).

Capture of methylated human DNA from patient stools. The MBD column was used to capture methylated human DNA in clinical stool samples from eight CRC patients and six normal individuals. Stool DNA was extracted, digested, and loaded on the MBD column in MBD buffer/0.52 M NaCl, and then washed with MBD buffer/0.6 M NaCl. Methylated DNA bound to the column was retrieved with MBD buffer/1.0 M NaCl, and prepared as above for amplifying methylated vimentin.

Real-time Alu PCR. Human DNA in patient stools was quantified using a real-time Alu PCR method as described elsewhere (Zou et al., Cancer Epidemiol. Biomarkers Prev., 15:1115-9 (2006)). Primers specific for the human Alu sequences, sense: (5' ACGCCTGTAATCCCAGCACTT 3' (SEQ ID NO:13); and antisense: 5' TCGCCCAGGCTG-GAGTGCA 3' (SEQ ID NO:14)), were used to amplify sequences about 245 bp inside Alu repeats (Zou et al., Cancer Epidemiol. Biomarkers Prev., 15:1115-9 (2006) and Zijlstra et al., Cancer Res., 62:7083-92 (2002)). Stool DNA was diluted 1 to 5 with nuclease-free water for PCR amplification. One μL water-diluted stool DNA was amplified in a total volume of 25 μL containing 1×iQ™ SYBR® Green Supermix (BioRad), 200 nM each primer under the following conditions: 95° C. for 3 minutes, followed by 23 cycles of 95° C. for 30 seconds, 60° C. for 30 seconds, and 72° C. for 40 seconds in a real-time iCycler (BioRad). Standard curve was created for each plate by amplifying 10-fold serially diluted human genomic DNA samples (Novagen, Madison, Wis.). Melting curve was made after each PCR reaction to guarantee that only one product was amplified for all samples. Amplification was carried out in 96-well plates in an iCycler (Bio-Rad). Each plate consisted of stool DNA samples and multiple positive and negative controls. Each assay was performed in duplicate.

Results

Separation of methylated cancer cell DNA from high background bacterial DNA. More tightly bound DNA requires elution with buffers at higher concentrations of NaCl. E. Coli DNA was amplified only in gradient MBD elutes with 0.4-0.6 M NaCl, but not in elutes with >0.6 M NaCl by either set of primers for the E. Coli genome. Methylated vimentin and TPEF were found mostly in MBD elutes with >0.6 M NaCl, and rarely in elutes with <0.6 M NaCl. Unmethylated vimentin was mainly in elutes with 0.4-0.72 M NaCl, and unmethylated TPEF was detected in almost all elutes with 0.4-1.0 M NaCl (FIG. 1).

Figure 2:
FIG. 2 is a photograph of gel with results for a simplified MBD buffer panel for an enrichment study. Stool DNA digested with Mse I was loaded to the column in MBD buffer/ 0.1M NaCl, and then sequentially eluted using MBD buffers with 0.2, 0.52, 0.6, and 1.0 M NaCl. DNA from each elute was amplified with primers for E. coli DNA. Lane 1, Flow through; Lane 2, 0.2 M; Lanes 3 and 4, 0.52M; Lane 5, 0.6 M; Lanes 6 and 7, 1.0 M; Lane 8, Positive control; Lane 9, Water control.

When stool DNA without spiked cell DNA was loaded to the column in MBD buffer/0.1M NaCl, and then sequentially eluted with MBD buffers with 0.2, 0.52, 0.6, and 1.0 M NaCl, most E. Coli DNA was eluted into buffers with ≦0.6 NaCl (FIG. 2). Less than 1% of total stool DNA was left in the 1.0 M NaCl elute when quantified with a photospectrometer.

As a buffer cutoff at 0.6 M NaCl separated methylated DNA from background bacterial DNA, a selected sequence of MBD buffers could be employed for the enrichment process. Stool DNA was loaded to MBD column in MBD buffer/0.52 M NaCl to allow the binding of most methylated human DNA, but little bacterial DNA. An additional MBD buffer/0.6 M NaCl further washed off loosely bound bacterial DNA and part of unmethylated human DNA. A last MBD buffer/1.0 M NaCl retrieved most methylated human DNA and part of unmethylated human DNA.

Figure 3:
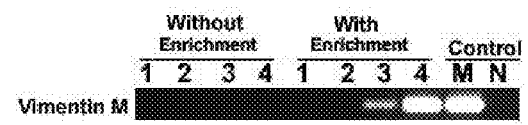
FIG. 3 is a photograph of gel with results demonstrating the capture of low amounts of methylated DNA spiked in stools. Cancer cell DNA (0, 2, 10, and 50 ng; RKO with SW480) was spiked into stool aliquots from a homogenized stool. Methylated vimentin was amplified with MSP in DNA samples from these stool aliquots with and without MBD enrichment. Lane 1, 0 ng; Lane 2, 2 ng; Lane 3, 10 ng; Lane 4, 50 ng.

Increased sensitivity of detecting methylated maker in spiked stool. With MBD enrichment, methylated vimentin was detectable in stool aliquots spiked with 10 and 50 ng RKO and SW480 cancer cell DNA, but not in those with 0 and 2 ng cancer cell DNA. Without MBD enrichment, methylated vimentin was not detectable in any stool aliquot with spiked DNA (FIG. 3).

Figure 4:
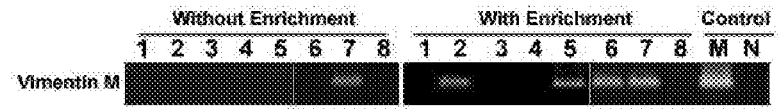
FIG. 4 is a photograph of gel with resulted demonstrating the capture of methylated human DNA in clinical stool samples. Eight stools from CRC patients with methylated tumor were used. Methylated vimentin was amplified with MSP in stool DNA with and without MBD enrichment. Human DNA amounts in eight stool DNA samples (lanes 1 to 8), quantified with real-time Alu PCR, were 1, 27, 0.5, 10, 4, 408, 832, and 2 ng, respectively.

Enhanced detection of methylated marker in patient stools. Vimentin was methylated in eight of the 14 paraffin-embedded CRC tissues. The eight stools with methylated tissues were used to test the sensitivity of MBD column. With MBD enrichment, methylated vimentin was detected in four CRC stool samples with 4, 27, 408, and 832 ng human DNA, but not in the other four samples with 0.5, 1, 2, and 10 ng of human DNA. Without MBD enrichment, methylated vimentin was detectable in only one CRC stool sample with 832 ng human DNA (FIG. 4). Methylated vimentin was not detected in six normal stools with or without MBD enrichment.

These results demonstrate that the methods and materials provided herein can be used to capture methylated human DNA from stool samples using methyl-CpG binding domain polypeptides chelated into a matrix (e.g., a nickel-agarose matrix in a chromatography column). With the enrichment of an MBD column, methylated vimentin could be detected by methylation-specific PCR in a stool model with as little as 10 ng of spiked human cancer cell DNA and in patient stool with only 4 ng total human DNA. When methylation-specific PCR was directly applied to crude stool DNA, methylated vimentin was only detectable in a stool sample which contained a large amount of human DNA (832 ng). As demonstrated herein, MBD polypeptides can have a very low affinity to bacterial DNA, which has a higher CG/AT ratio than human genomic DNA and is densely methylated at cytosine and adenine residues by Dcm and Dam methyltransferase (Palmer and Marinus, *Gene,* 143:1-12 (1994)). Bacterial DNA fragments can be eluted into buffers at concentrations below 0.6 M sodium chloride. Methylated human DNA was enriched about 100 fold by the MBD column without interference by the abundant bacterial DNA in stool. These results demonstrate that capturing methylated CpG islands with an MBD polypeptide can increase the detection sensitivity of stool-based methylated marker assays, even in stools with low concentrations of template human DNA and high amount of methylated bacterial DNA.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for enriching methylated mammalian nucleic acid if present in a stool sample, wherein said method comprises:
   (a) contacting nucleic acid from a stool sample with an MBD polypeptide to form a nucleic acid-MBD polypeptide complex;
   (b) eluting bacterial nucleic acid from said MBD polypeptide of the formed nucleic acid-MBD polypeptide complex using a buffer with less than or equal to 0.6 M NaCl, and
   (c) eluting methylated mammalian nucleic acid from said complex if said stool sample contained methylated mammalian nucleic acid using a buffer with greater than 0.6 M NaCl, thereby forming an enriched, methylated mammalian nucleic acid sample.

2. The method of claim 1, wherein said MBD polypeptide is a human or rat MBD polypeptide.

3. The method of claim 1, wherein said enriched, methylated mammalian nucleic acid sample comprises a higher ratio of methylated mammalian nucleic acid to methylated bacterial nucleic acid than the ratio of methylated mammalian nucleic acid to methylated bacterial nucleic acid present in said stool sample.

4. A method for detecting a colorectal or supracolonic aerodigestive neoplasm in a mammal, said method comprising:
   (a) contacting nucleic acid from a stool sample from said mammal with an MBD polypeptide to form a nucleic acid-MBD polypeptide complex;
   (b) eluting bacterial nucleic acid from said MBD polypeptide of the formed nucleic acid-MBD polypeptide complex using a buffer with less than or equal to 0.6 M NaCl;
   (c) eluting methylated mammalian nucleic acid from said complex if said stool sample contained methylated mammalian nucleic acid using a buffer with greater than 0.6 M NaCl, thereby forming an enriched, methylated mammalian nucleic acid sample if said stool sample contained methylated mammalian nucleic acid; and
   (d) determining whether or not said enriched, methylated mammalian nucleic acid sample comprises a methylated mammalian nucleic acid marker indicative of said colonic or supracolonic aerodigestive neoplasm, wherein the presence of said marker indicates that said mammal has said colonic or supracolonic aerodigestive neoplasm.

5. The method of claim 4, wherein said neoplasm comprises a premalignant neoplasm.

6. The method of claim 4, wherein said neoplasm comprises a malignant neoplasm.

7. The method of claim 4, wherein said neoplasm is a colorectal neoplasm.

8. The method of claim 4, wherein said neoplasm is a supracolonic aerodigestive neoplasm.

9. The method of claim 8, wherein said supracolonic aerodigestive neoplasm is selected from the group consisting of small intestine, gall bladder, bile duct, pancreas, liver, stomach, esophagus, lung, tracheal-bronchial, and naso-oro-pharyngeal neoplasms.

10. A method for enriching methylated mammalian nucleic acid if present in a stool sample, wherein said method comprises:
    (a) contacting nucleic acid from a stool sample with an MBD polypeptide to form a nucleic acid-MBD polypeptide complex;
    (b) eluting bacterial nucleic acid from said MBD polypeptide of the formed nucleic acid-MBD polypeptide complex using a buffer with less than or equal to 0.6 M NaCl; and
    (c) eluting methylated mammalian nucleic acid from said complex if said stool sample contained methylated mammalian nucleic acid to obtain an enriched, methylated mammalian nucleic acid sample comprising a higher ratio of methylated mammalian nucleic acid to methylated bacterial nucleic acid than the ratio of methylated mammalian nucleic acid to methylated bacterial nucleic acid present in said stool sample, wherein said eluting step comprises eluting said methylated mammalian nucleic acid from said complex using a buffer with greater than 0.6 M NaCl.

11. The method of claim 10, wherein said MBD polypeptide is a human or rat MBD polypeptide.

* * * * *

SEQUENCE LISTING

```
<160> NUMBER OF SEQ ID NOS: 14

<210> SEQ ID NO 1
<211> LENGTH: 27
<212> TYPE: DNA
<213> ORGANISM: Homo sapiens

<400> SEQUENCE: 1
tcgtttcgag gttttcgcgt tagagac                                        27

<210> SEQ ID NO 2
<211> LENGTH: 25
<212> TYPE: DNA
<213> ORGANISM: Homo sapiens

<400> SEQUENCE: 2
cgactaaaac tcgaccgact cgcga                                          25

<210> SEQ ID NO 3
<211> LENGTH: 25
<212> TYPE: DNA
<213> ORGANISM: Homo sapiens

<400> SEQUENCE: 3
ttggtggatt ttttgttggt tgatg                                          25

<210> SEQ ID NO 4
<211> LENGTH: 30
<212> TYPE: DNA
<213> ORGANISM: Homo sapiens

<400> SEQUENCE: 4
cacaacttac cttaaccctt aaactactca                                     30

<210> SEQ ID NO 5
<211> LENGTH: 25
<212> TYPE: DNA
<213> ORGANISM: Homo sapiens

<400> SEQUENCE: 5
cggtaaagat tcgagtaagg aacgt                                          25

<210> SEQ ID NO 6
<211> LENGTH: 25
<212> TYPE: DNA
<213> ORGANISM: Homo sapiens

<400> SEQUENCE: 6
aaaacatcga ccgaacaacg acgtc                                          25
```

```
<210> SEQ ID NO 7
<211> LENGTH: 30
<212> TYPE: DNA
<213> ORGANISM: Homo sapiens

<400> SEQUENCE: 7
gttatttggt aaagatttga gtaaggaatg                              30

<210> SEQ ID NO 8
<211> LENGTH: 25
<212> TYPE: DNA
<213> ORGANISM: Homo sapiens

<400> SEQUENCE: 8
aaaacatcaa ccaaacaaca acatc                                  25

<210> SEQ ID NO 9
<211> LENGTH: 20
<212> TYPE: DNA
<213> ORGANISM: Escherichia coli

<400> SEQUENCE: 9
gtgccggatt agccaactta                                        20

<210> SEQ ID NO 10
<211> LENGTH: 20
<212> TYPE: DNA
<213> ORGANISM: Escherichia coli

<400> SEQUENCE: 10
gtgacgattc cagccgtact                                        20

<210> SEQ ID NO 11
<211> LENGTH: 20
<212> TYPE: DNA
<213> ORGANISM: Escherichia coli

<400> SEQUENCE: 11
actcctgcga aacatcatcc                                        20

<210> SEQ ID NO 12
<211> LENGTH: 20
<212> TYPE: DNA
<213> ORGANISM: Escherichia coli

<400> SEQUENCE: 12
cggcaccttg ctaagtcttc                                        20

<210> SEQ ID NO 13
<211> LENGTH: 21
<212> TYPE: DNA
<213> ORGANISM: Homo sapiens

<400> SEQUENCE: 13
acgcctgtaa tcccagcact t                                      21

<210> SEQ ID NO 14
<211> LENGTH: 19
<212> TYPE: DNA
<213> ORGANISM: Homo sapiens

<400> SEQUENCE: 14
tcgcccaggc tggagtgca                                         19
```